(12) United States Patent
Kalvins et al.

(10) Patent No.: US 8,791,273 B2
(45) Date of Patent: Jul. 29, 2014

(54) 4R,5S-ENANTIOMER OF 2-(5-METHYL-2-OXO-4-PHENYL-PYRROLIDIN-1-YL)-ACETAMIDE WITH NOOTROPIC ACTIVITY

(75) Inventors: Ivars Kalvins, Ikskile (LV); Antons Lebedevs, Riga (LV); Aleksandrs Cernobrovijs, Riga (LV); Maija Dambrova, Riga (LV); Liga Zvejniece, Marupe (LV); Maksims Vorona, Riga (LV); Grigorijs Veinbergs, Riga (LV)

(73) Assignee: JSC Grindeks, Riga (LV)

( * ) Notice: Subject to any disclaimer, the term of this patent is extended or adjusted under 35 U.S.C. 154(b) by 0 days.

(21) Appl. No.: 13/508,184

(22) PCT Filed: Nov. 4, 2010

(86) PCT No.: PCT/EP2010/066767
§ 371 (c)(1),
(2), (4) Date: May 4, 2012

(87) PCT Pub. No.: WO2011/054888
PCT Pub. Date: May 12, 2011

(65) Prior Publication Data
US 2012/0215010 A1 Aug. 23, 2012

(30) Foreign Application Priority Data
Nov. 5, 2009 (LV) ..................... P-09-193

(51) Int. Cl.
*C07D 207/27* (2006.01)

(52) U.S. Cl.
CPC .................. *C07D 207/27* (2013.01)
USPC .......................................... 548/550

(58) Field of Classification Search
CPC ..................................... C07D 207/27
USPC ............................................. 548/550
See application file for complete search history.

(56) References Cited

FOREIGN PATENT DOCUMENTS

WO WO2007/104780 9/2007

OTHER PUBLICATIONS

Altman, BMJ. Jan. 25, 2003; 326(7382): 219.*
Berestovitskaya, V.M., et al., Proceedings of the I International Conference on the Chemistry and Biological Acivity of Nitrogen-Containing Heterocycles and Alkaloids, vol. 1, Oct. 9-12, 2011, 216-220.
Cologne, J., et al., "No. 115" Bulletin de la Societe Chimique de France, p. 598-603, Jan. 1, 1962.
International Search Report for PCT/EP2010/066767 of January 27, 2011.
Langlois, M., et al., "No. 409" Bulletin de la Societe Chimique de France, No. 8, p. 2976-2982, Aug. 1, 1971.

* cited by examiner

*Primary Examiner* — Robert Havlin
(74) *Attorney, Agent, or Firm* — Hueschen and Sage

(57) ABSTRACT

The invention relates to the 5S,4R-enantiomer of 2-(5-methyl-2-oxo-4-phenyl-pyrrolidin-1-yl)-acetamide with cognition enhancing activity of high pharmacological value and to its preparation method which includes the synthesis of 5S-methyl-4R-phenylpyrrolidin-2-one, its N-alkylation with ethyl haloacetate and the treatment of intermediate ethyl 2-(5S-methyl-2-oxo-4R-phenyl-pyrrolidin-1-yl)-acetate with ammonia.

12 Claims, No Drawings

4R,5S-ENANTIOMER OF 2-(5-METHYL-2-OXO-4-PHENYL-PYRROLIDIN-1-YL)-ACETAMIDE WITH NOOTROPIC ACTIVITY

TECHNICAL FIELD

This invention relates to preparation and medical use of 4R,5S-enantiomer of 2-(5-methyl-2-oxo-4-phenylpyrrolidin-1-yl)-acetamide for use as nootropic medicament.

BACKGROUND ART

It is known that cognition enhancing drugs facilitate attention abilities and acquisition, storage and retrieval of information and attenuate the impairment of cognitive functions associated with head traumas, stroke, age and age-related pathologies.

Racemic molecule of 2-(5-methyl-2-oxo-4-phenyl-pyrrolidin-1-yl)-acetamide, a piracetam structural derivative, was mentioned in 2001 (M. V. Berestovitskaya, M. M. Zobachova, B. M. Novikov, O. S. Vasil'eva, N. V. Usik, S. M. Aleksandrova, I. N. Turenkov. International Conference on the Synthesis of Nitrogen Heterocycles, Moscov, Oct. 9-12, 2001, vol. 1, pp. 229-233). However there is no data on the chemical structure and biological properties of this compound provided.

EP 2013166 B (AKCIJU SABIEDRIBA OLAINFARM) Oct. 3, 2010 disclosed R-enantiomer of N-carbamoylmethyl-4-phenyl-2-pyrrolidinone being different from the present one only in that 5-methyl group is lacking with neurotropic activity.

SUMMARY OF INVENTION

According to the current invention, the pharmacological studies of racemic 2-(5-methyl-2-oxo-4-phenyl-pyrrolidin-1-yl)acetamide, containing two chiral centers in positions 4 and 5 of the pyrrolidone ring, unexpectedly revealed its rather promising cognition enhancing properties. However, when we have prepared separate 4R,5S-enantiomer of 2-(5-methyl-2-oxo-4-phenyl-pyrrolidin-1-yl)-acetamide and subjected it to nootropic investigation, it surprisingly and unexpectedly appeared to be much more pharmacologically active in comparison to the parent racemic compound.

According to the current invention, we describe a method of preparation of 4R,5S-enantiomer of 2-(5-methyl-2-oxo-4-phenyl-pyrrolidin-1-yl)-acetamide of Formula 1 with cognition enhancing properties of high pharmacological value:

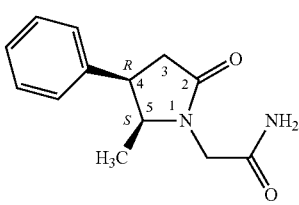

which is a new chemical compound with nootropic activity.

According to the current invention, the chemical scheme of 2-(5S-methyl-2-oxo-4R-phenyl-pyrrolidin-1-yl)-acetamide (1) preparation includes the synthesis of 4R,5S-enantiomer of 5-methyl-4-phenylpyrrolidin-2-one (2) and the insertion of acetamide group in position 1 of the pyrrolidone ring:

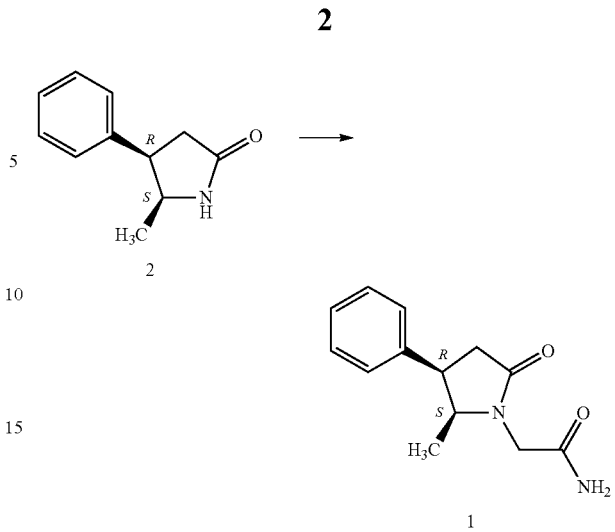

Methods of racemic 5-methyl-4-phenylpyrrolidin-2-one preparation and its separation into enantiomeric mixture of eritro- and treo-isomres were documented in literature (Colonge J., Pouchol J. M., *Bull. Soc. Chim.*, 1962, 598-603; Langlois M. et. al. *Bull. Soc. Chim.*, 1971, 2976-2982; Lesniak S., Pasternak B., *Tetrahedron Lett.*, 2005, 46, 3093-3095). However, no any written evidence about the resolution of racemic 5-methyl-4-phenylpyrrolidin-2-one into separate enantiomers or their direct synthesis from chiral or non-chiral chemical substances have been found.

According to the current invention, this problem was solved by asymmetric Michael addition of 2-nitroprop-1-enylbenzene (3) to diethyl malonate (3) in the presence of complex catalyst consisting of chiral 2,2'-cyclopropylidene-bis-oxazoline 5, magnesium triflate and organic base leading to the formation of diethyl 2-[2(R,S)-nitro-1R-phenylpropyl]-malonate diastereoisomeric mixture (6)

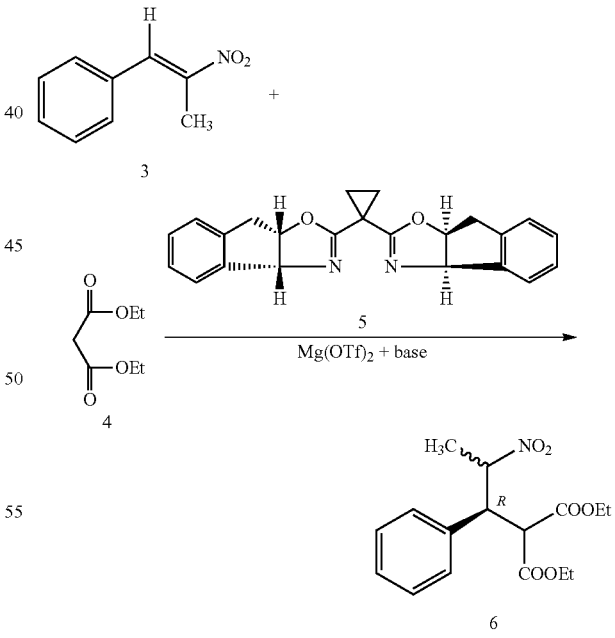

The obtained intermediate 6 was converted into 5S-methyl-4R-phenylpyrrolidin-2-one (2) by the sequence of following steps (see scheme below):

a) the addition of 2-nitroprop-1-enylbenzene to diethyl malonate in the presence of complex catalysts consisting of chiral 2,2'-cyclopropylidene-bis-oxazoline, magnesium triflate and organic base;

b) the conversion of diethyl 2-(2-nitro-1R-phenylpropyl) malonate into enantiomeric 5S-methyl-4R-phenylpyrrolidin-2-one by the hydrogenation of diethyl 2-(2-nitro-1R-phenyl-propyl)malonate in the presence of Ni Reney, resolution of the diastereoisomeric mixture of ethyl 5-methyl-2-oxo-4(R)-phenylpyrrolidin-3(S)-carboxylate into separate 5S,4R- and 5R,4-enantiomers, decarboxylation of ethyl 5(S)-methyl-2-oxo-4(R)-phenylpyrrolidin-3(S)-carboxylate;

c) the substitution of hydrogen in the amide group of 5S-methyl-4R-phenylpyrrolidin-2-one with sodium ion in a suitable organic solvent.

d) the N-alkylation of N-metalated 5S-methyl-4R-phenylpyrrolidin-2-one with haloacetic acid esters in a suitable organic solvent;

e) the amidation of ethyl 2-(5S-methyl-2-oxo-4R-phenyl-pyrrolidin-1-yl)-acetate with ammonia in a suitable solvent.

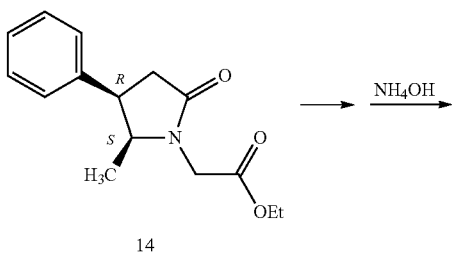

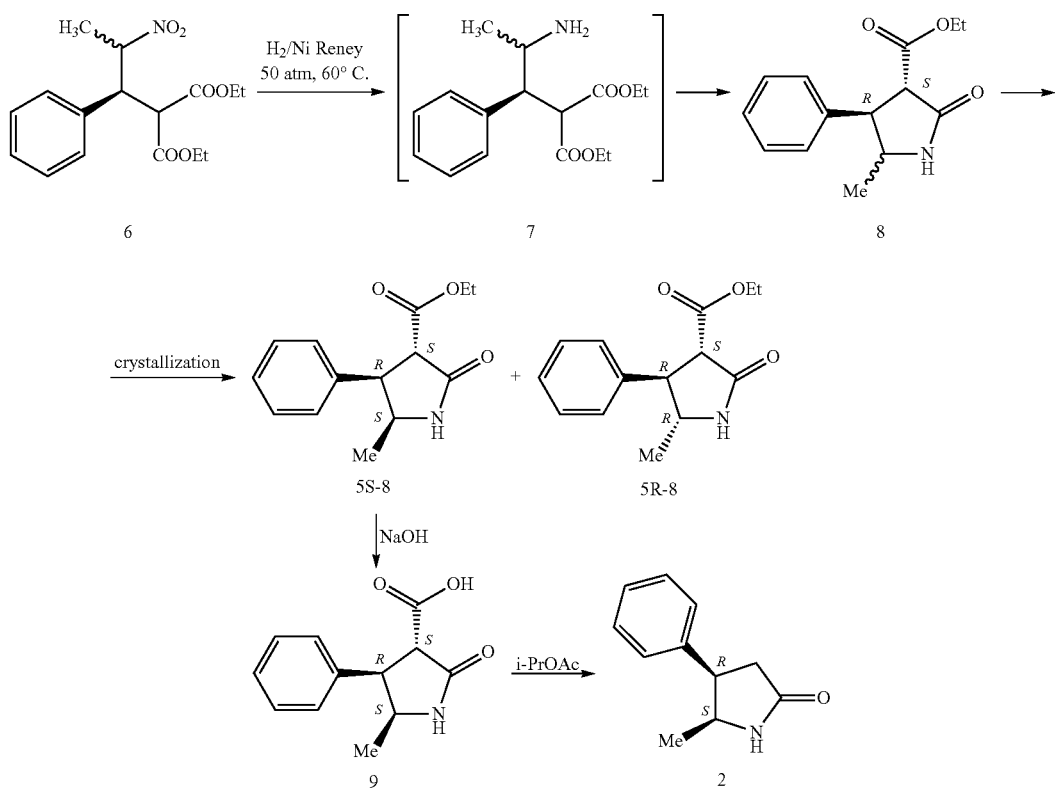

Conversion of 5S-methyl-4R-phenylpyrrolidin-2-one (2) into 2-(5S-methyl-2-oxo-4R-phenyl-pyrrolidin-1-yl)-acetamide (1) included the substitution of hydrogen in NH group of 2 with sodium, alkylation of metalated pyrrolidin-2-one 13 with haloacetic acid ethyl ester and treatment of the intermediate ethyl 2-(5S-methyl-2-oxo-4R-phenylpyrrolidin-1-yl)-acetate (14) with ammonia in a suitable solvent.

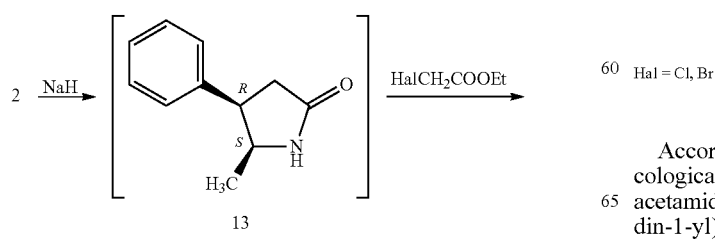

Hal = Cl, Br

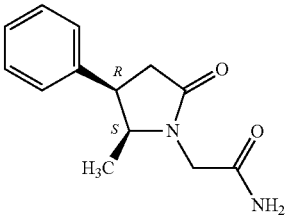

According to the current invention, comparative pharmacological evaluation of 2-(4R-phenyl-2-oxopyrrolidin-1-yl) acetamide), racemic 2-(5-methyl-2-oxo-4-phenyl-pyrrolidin-1-yl)acetamide and 2-(5S-methyl-2-oxo-4R-phenyl-pyrrolidin-1-yl)-acetamide, employing standard passive avoidance test, proved the high effectiveness of the optically active 2-(5S-methyl-2-oxo-4R-phenylpyrrolidin-1-yl)-acetamide (1) as enhancer of learning memory.

Therefore, 2-(5S-methyl-2-oxo-4R-phenyl-pyrrolidin-1-yl)acetamide may be used as a highly effective agent for use as medicament with nootropic activity.

DESCRIPTION OF EMBODIMENTS

The scope of the invention should not be limited to the working examples, which are for demonstration purposes. One skilled in the art can practice the invention based on the disclosures in the present patent application.

The following examples are illustrating but not restricting the present invention.

EXAMPLES

Example 1

The solution of (3aR,3'aR,8aS,8'aS)-2,2'-cyclopropylidenebis-[3a,8a]-dihydro-8H-indeno-[1,2-d]-oxazole (420 mg, 1.18 mM) in chloroform (hydrocarbon stabilized) (5 ml), magnesium triflate (378 mg, 0. 1.18 mM) and water (25 µL) were added into 250 ml reaction flask at room temperature and mixture was stirred under argon for 1 hour. Molecular sieves (1.0 g) and 1,4-dioxane (30 ml) were added to the obtained mixture, and stirred for additional 30 min. Obtained suspension was diluted with 45 ml of chloroform solution containing diethylmalonate (1.67 g, 10.2 mM), 2-nitroprop-1-enylbenzene (1.63 g, 10.0 mM) and morpholine (46 µL). Reaction mixture was stirred at room temperature. Conversion and selectivity were determined by chiral HPLC analysis [Chiralpak IC, 4.6×250 mm, 1.0 ml/min, eluent i-PrOH-Hexane (1:9)] each 24 hours. After completion of reaction, the reaction mixture was diluted with hexane (50 ml), stirred for 20 min. and the solid was filtered off. The filtrate was washed with 5% aqueous HCl (2×50 ml), brine (2×50 ml), dried over anhydrous $Na_2SO_4$. The drying reagent was removed by filtration and the solution was concentrated under reduced pressure. The residue was purified by column chromatography on silica with ethylacetate/hexane (1:10) collecting fractions with $R_f$ 0.28. Yield 87% (2.8 g). Obtained low-melting yellow solid, according to chiral HPLS is the mixture of eritro- and treo-isomers of diethyl 2-(2-nitro-1R-phenylpropyl)-malonate in ratio 3:1. Optical purity: 93%.

$^1$H NMR ($CDCl_3$), δ, ppm (J, Hz): 0.85 (2.25H, t, J=7.0 eritro-$CH_2\underline{CH_3}$); 0.93 (0.75H, t, J=7.0 treo-$CH_2\underline{CH_3}$); 1.15-1.27 (3H, m, $CH_2\underline{CH_3}$); 1.29 (0.75H, d, J=6.8, treo-C$\underline{H_3}CNO_2$); 1.37 (2.25H, d, J=6.8, eritro-C$\underline{H_3}CNO_2$); 3.63-3.93 (3H, m, $\underline{CH_2}CH_3$, COC$\underline{H}$CO); 4.07-4.29 (3H, m, $\underline{CH_2}CH_3$, PhC$\underline{H}$,); 4.29-5.06 (0.25H, m, treo-C$\underline{H}NO_2$); 5.07-5.16 (0.75H, m, eritro-C$\underline{H}NO_2$); 6.99-7.28 (5H, m, $C_6H_5$).

Example 2

The substitution of morpholine in example 1 by N-methylmorpholine resulted in the formation of diethyl 2-(2-nitro-1R-phenylpropyl)-malonate as a mixture of eritro- and treo-isomers 3:1. Optical purity: 94%. Yield 85%.

Example 3

The substitution of morpholine in example 1 by the mixture of morpholine (46 µL) and tetra-methylguanidine (46 µL) resulted in the formation of diethyl 2-(2-nitro-1R-phenylpropyl)-malonate as a mixture of eritro- and treo-isomers 3:1. Optical purity: 95%. Yield 87%.

Example 4

The stirring suspension of diethyl 2-(2-nitro-1R-phenylpropyl)-malonate (2.34 g, 7.22 mM) in ethanol (50 ml) and 1 ml of 50% Ni Reney slurry in water was hydrogenated at 50° C. and 50 atm for 18 hours. After completion of reaction, the reaction mixture was cooled, the catalyst was filtered off and washed with 30 ml of ethanol. Filtrate was concentrated under reduced pressure. The residue was purified by liquid column chromatography on silica gel with $CH_2Cl_2$/EtOH (10:1→1:10) collecting fractions with $R_f$ 0.28. Yield 80% (1.43 g). Obtained white solid according to $^1$H NMR spectra is the mixture of eritro- and treo-isomers of ethyl 5-methyl-2-oxo-4(R)-phenylpyrrolidin-3(S)-carboxylate in ratio 17:3. Yield 80% (1.43 g).

$^1$H NMR ($CDCl_3$), δ, ppm (J, Hz): 0.76 (2.55H, d, J=6.3 eritro-5-$CH_3$); 1.18-1.23 (3.45H, m, treo-5-$CH_3$ and $CH_2\underline{CH_3}$); 3.73 (1H, d, J=9.0, 3-H); 4.02-4.22 (4H, m, $\underline{CH_2}CH_3$, 4-H, 5-H); 6.23 (1H, br. s, NH); 7.09-7.33 (5H, m, $C_6H_5$).

Recrystallization of the obtained product from ethanol resulted in the isolation of 785 mg of 5S-methyl-4R-phenyl-2-pyrrolidinone-3S-carboxylate. M. p. 141-143° C.

Anal. Calculated for $C_{14}H_{17}NO_3$ (247.30) C, 68.00; H, 6.93; N, 5.66.

Found: C, 67.93; H, 6.87; N, 5.64.

$^1$H NMR ($CDCl_3$), δ, ppm (J, Hz): 0.76 (3H, d, J=6.3 eritro-5-$CH_3$); 1.18-1.23 (3H, m, $CH_2\underline{CH_3}$); 3.73 (1H, d, J=9.0, 3-H); 4.02-4.22 (4H, m, $\underline{CH_2}CH_3$, 4-H, 5-H); 6.23 (1H, br. s, NH); 7.09-7.33 (5H, m, $C_6H_5$).

Example 5

Potassium hydroxide (672 mg, 12 mM) was added to the solution of ethyl 5S-methyl-4R-phenyl-2-pyrrolidinone-3S-carboxylate (900 mg, 4.00 mM) in methanol (50 ml) and obtained mixture was refluxed for 3 hours. The reaction mixture was cooled and evaporated under reduced pressure. The residue was dissolved in 20 ml of water, water solution was washed with ethylacetate (3×30 ml) adjusted to pH 2 with diluted HCl and evaporated under reduced pressure. Obtained residue was suspended in EtOH/$CH_2Cl_2$ (1:1) solution, stirred for 1 hour, filtered and filtrate evaporated under reduced pressure. The residue was dissolved in the solution of iso-propylacetate (40 ml) and para-toluenesulfonic acid (100 mg). Obtained mixture was refluxed for 24 hours, cooled and concentrated under reduced pressure. The residue was purified by liquid column chromatography on silica gel with $CH_2Cl_2$/EtOH (20:1) collecting fractions with $R_f$ 0.40. Obtained yellow solid according chiral HPLC is the eritro-somer of 5S-methyl-4R-phenylpyrrolidin-2-one. Yield 65% (455 mg).

Anal. Calculated for $C_{11}H_{13}NO$ (175.23) C, 75.40; H, 7.48; N, 7.99.

Found: C, 75.63; H, 7.55; N, 8.07.

$^1$H NMR ($CDCl_3$), δ, ppm (J, Hz): 0.75 (3.00H, d, J=6.5 5-$CH_3$); 2.55-2.69 (2H, m, 3-$CH_2$); 3.64-3.72 (1H, m, 4-H); 3.96-4.04 (1H, m, 5-H); 6.78 (1H, br. s, NH); 7.07-7.33 (5H, m, $C_6H_5$).

Example 6

The substitution of potassium hydroxide in example 5 by sodium hydroxide resulted in the formation of the 5S-methyl-4R-phenyl-2-pyrrolidinone. Yield 62%.

Example 7

The solution of 5S-methyl-4R-phenyl-2-pyrrolidinone (351 mg, 2.00 mM) in toluene (30 ml) was added to the suspension of sodium hydride (56 mg, 2.35 mM) in toluene (30 ml). The stirred mixture was heated at 80÷90° C. during 30 min and then cooled to the room temperature. Ethyl bromoacetate (368 mg, 2.20 mM) was added to the reaction mixture, which was heated at 110÷120° C. for 6 hours and than concentrated under reduced pressure. The residue was dissolved in toluene (30 ml). Obtained solution was washed with 5% aqueous HCl (2×50 ml), brine (2×50 ml), dried over anhydrous $Na_2SO_4$. The drying reagent was removed by filtration and the solution was concentrated under reduced pressure. The residue was purified by column chromatography on silica with $CH_2Cl_2$/MeOH (20:1). Fractions with $R_f$0.48 were collected and evaporated under reduced pressure, giving ethyl 2-(5S-methyl-2-oxo-4R-phenyl-pyrrolidin-1-yl)-acetate (381 mg, 73%) as colorless oil.

$^1$H NMR ($CDCl_3$), δ, ppm (J, Hz): 0.72 (3.00H, d, J=6.6 5-$CH_3$); 1.23 (3H, t, J=7.0, $CH_2\underline{CH_3}$); 2.60-2.91 (2H, d, J=8.5, 3-$CH_2$); 3.65-3.74 (1H, m, 4-H); 3.66 (2H, d, J=17.7, $NCH_2COO$); 4.01-4.10 (1H, m, 5-H); 4.10-4.20 (2H, m, $\underline{CH_2}CH_3$); 4.38 (1H, d, J=17.7, $NCH_2COO$); 7.09-7.31 (5H, m, $C_6H_5$).

Example 8

The substitution of sodium hydride in example 7 by sodium ethylate resulted in the formation of ethyl 2-(5S-methyl-2-oxo-4R-phenyl-pyrrolidin-1-yl)-acetate with yield 68%.

Example 9

The substitution of ethyl bromoacetate in example 7 by ethyl chloroacetate resulted in formation of ethyl 2-(5S-methyl-2-oxo-4R-phenyl-pyrrolidin-1-yl)-acetate with yield 70%.

Example 10

The substitution of toluene in example 7 by hexane resulted in the formation of ethyl 2-(5S-methyl-2-oxo-4R-phenyl-pyrrolidin-1-yl)-acetate with yield 71%.

Example 11

The substitution of toluene in example 7 by benzene resulted in the formation of ethyl 2-(5S-methyl-2-oxo-4R-phenyl-pyrrolidin-1-yl)-acetate with yield 70%.

Example 12

The substitution of toluene in example 7 by 1,4-dioxane resulted in the formation of ethyl 2-(5S-methyl-2-oxo-4R-phenyl-pyrrolidin-1-yl)-acetate with yield 72%.

Example 13

The substitution of toluene in example 7 by dichloromethane resulted in the formation of ethyl 2-(5S-methyl-2-oxo-4R-phenyl-pyrrolidin-1-yl)-acetate with yield 67%.

Example 14

The solution of ethyl 2-(5S-methyl-2-oxo-4R-phenyl-pyrrolidin-1-yl)-acetate (350 mg, 1.34 mM) in methanol (30 ml) was saturated with gaseous ammonia for 5 hours. Reaction mixture was concentrated under reduced pressure and residue was purified by column chromatography with $CH_2Cl_2$/EtOH (20:1). Fractions with $R_f$0.32 were collected and evaporated under reduced pressure, giving 2-(5S-methyl-2-oxo-4R-phenyl-pyrrolidin-1-yl)-acetamide. (249 mg, 80%) as white solid recrystallized from water. M.p. 169-171° C.

Calculated for $C_{13}H_{16}N_2O_2$ (232.28) C, 67.22; H, 6.94; N, 12.06.

Found: C, 67.31; H, 6.99; N, 12.10.

$^1$H NMR ($CDCl_3$), δ: 0.77 (3.00H, d, J=6.6 5-$CH_3$); 2.62-2.81 (2H, m, 3-$CH_2$); 3.66-3.75 (1H, m, 4-H); 3.75 (1H, d, J=16, $NCH_2COO$); 3.98-4.08 (1H, m, 5-H); 4.04 (1H, d, J=16, $NCH_2COO$); 5.48 and 6.29 (2H, br.s, br.s, $NH_2$); 7.07-7.32 (5H, m, $C_6H_5$).

Example 15

The substitution of gaseous ammonia in example 13 by the 25% aqueous ammonium resulted in the formation of 2-(5S-methyl-2-oxo-4R-phenyl-pyrrolidin-1-yl)-acetamide with 78% yield.

Example 16

The substitution of methanol in example 13 by the ethanol resulted in the formation of 2-(5S-methyl-2-oxo-4R-phenyl-pyrrolidin-1-yl)-acetamide with 81% yield.

Example 17

The substitution of methanol in example 13 by the n-propanol resulted in the formation of 2-(5S-methyl-2-oxo-4R-phenyl-pyrrolidin-1-yl)-acetamide with 77% yield.

Example 18

Racemic 2-(5-methyl-2-oxo-4-phenyl-pyrrolidin-1-yl)-acetamide was prepared by N-methycarbamoylation of 5-methyl-4-phenylpyrrolidin-2-one $^1$H NMR ($CDCl_3$), δ: 0.77 (1.50H, d, J=6.6 eritro-5-$CH_3$); 1.23 (1.50H, d, J=6.3 treo-5-$CH_3$); 2.53-2.86 (2H, m, 3-$CH_2$); 3.66-3.75 (1H, m, 4-H); 3.75 (0.5H, d, J=16, eritro-$NCH_2COO$); 3.86 (0.5H, d, J=16, treo-$NCH_2COO$); 3.95 (0.5H, d, J=16, treo-$NCH_2COO$); 3.98-4.08 (1H, m, 5-H); 4.04 (0.5H, d, J=16, erito-$NCH_2COO$); 5.48 and 6.29 (2H, br.s, br.s, $NH_2$); 7.07-7.32 (5H, m, $C_6H_5$).

Biological Tests

Learning and Memory

Passive avoidance test was performed in a shuttle-box apparatus (Ugo Basile, Italy) with two communicating compartments of equal size (20×10×16 cm) and a stainless steel grid floor (bars spaced 0.7 cm apart). The right-hand compartment (shock compartment) was painted black to obtain a dark chamber. The left-hand compartment was painted white and illuminated by a bulb (100 W) installed on the top of plexiglass cover. These compartments were separated by a guillotine door (5×4 cm). On day 1 (training trial), mice were placed in the illuminated compartment and the door between the two compartments was opened 60 s later. When mice entered the dark compartment with all four feet, the door automatically closed and an inescapable electrical foot shock (0.1 mA; 3 s) was delivered through the grid floor. Latency to cross into the dark compartment (training latency) was automatically measured. The retention test was performed 24 hours later (day 2). Mice were placed into the light (safe) compartment, with access to the dark one (within 10 s) for a period of 300 s (cut-off time). The latency to cross into the dark compartment with all four feet was automatically measured (retention latency).

Effects of 2-(4R-phenyl-2-oxopyrrolidin-1-yl)acetamide), racemic 2-(5-methyl-2-oxo-4-phenyl-pyrrolidin-1-yl)-acetamide and 2-(5S-methyl-2-oxo-4R-phenyl-pyrrolidin-1-yl)-acetamide on retention of passive avoidance response (memory) in ICR male mice.

Data presented in Table 1 demonstrate effects of, 2-(4R-phenyl-2-oxopyrrolidin-1-yl)acetamide), racemic 2-(5-methyl-2-oxo-4-phenyl-pyrrolidin-1-yl)-acetamide and 2-(5S-methyl-2-oxo-4R-phenyl-pyrrolidin-1-yl)-acetamide on memory in the passive avoidance task in mice.

TABLE 1

Effects of administrated compounds on memory in the passive avoidance task in mice

| Compounds | Latent time, s |
| --- | --- |
| Control (Saline) | 62.7 ± 6.2 |
| 2-(4R-phenyl-2-oxopyrrolidin-1-yl)acetamide | 94.9 ± 27.6 |
| 2-(5-methyl-2-oxo-4-phenyl-pyrrolidin-1-yl)-acetamide racemic | 74.2 ± 19.9 |
| 2-(5S-methyl-2-oxo-4R-phenyl-pyrrolidin-1-yl)-acetamide | 170.6 ± 41.9* #$ |

The compounds were administered intraperitoneally at the dose of 46 µmol/kg 60 min before the training trial (day 1). The saline control group was run concurrently with the drug-treated groups. The statistical analysis was performed by Student's t-test. Data represent mean±S.E.M
*$p<0.05$, #$p<0.05$, $$p<0.05$ versus saline control group, 2-(4R-phenyl-2-oxopyrrolidin-1-yl)acetamide-treated group and racemic2-(5-methyl-2-oxo-4-phenyl-pyrrolidin-1-yl)-acetamide-treated group, respectively; n≥10

As it is presented in Table 1, 2-(5S-methyl-2-oxo-4R-phenyl-pyrrolidin-1-yl)-acetamide treatment at the dose of 46 µmol/kg induced a statistically significant effect on memory.

The invention claimed is:

1. A process of preparation of 2-(5S-Methyl-2-oxo-4R-phenyl-pyrrolidin-1-yl)-acetamide of Formula I

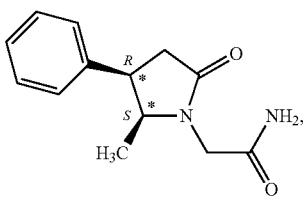

I comprising the following steps:
a) addition of 2-nitroprop-1-enylbenzene to diethyl malonate in the presence of complex catalysts consisting of a chiral 2,2'-cyclopropylidene-bis-oxazoline, magnesium triflate and an organic base;
b) conversion of diethyl 2-(2-nitro-1R-phenylpropyl)malonate obtained in step a) into enantiomeric 5S-methyl-4R-phenylpyrrolidin-2-one via hydrogenation of diethyl 2-(2-nitro-1R-phenylpropyl)malonate in the presence of Raney Ni at a hydrogen pressure between 3 and 60 atm to obtain a diastereoisomeric mixture of ethyl 5-methyl-2-oxo-4(R)-phenylpyrrolidin-3(S)-carboxylate, resolution of the diastereoisomeric mixture of ethyl 5-methyl-2-oxo-4(R)-phenylpyrrolidin-3(S)-carboxylate thus obtained into separate 5S,4R- and 5R,4-enantiomers, and decarboxylation of ethyl 5(S)-methyl-2-oxo-4(R)-phenylpyrrolidin-3(S)-carboxylate;
c) substitution of hydrogen in the amide group of 5S-methyl-4R-phenylpyrrolidin-2-one obtained in step b) with sodium on in a suitable organic solvent;
d) alkylation of N-metalated 5S-methyl-4R-phenylpyrrolidin-2-one obtained in step c) with a haloacetic acid ester in a suitable organic solvent; and
e) amidation of ethyl 2-(5S-methyl-2-oxo-4R-phenyl-pyrrolidin-1-yl)-acetate obtained in step d) with ammonia in a suitable solvent.

2. The process according to claim 1, wherein, in step a), chiral 2,2'-cyclopropylidene-bis(oxazoline) is (3aR,3'aR,8aS,8'aS)-2,2'-cyclopropylidenebis-[3a,8a]-dihydro-8H-indeno-[1,2-d]-oxazole.

3. The process according to claim 1, wherein, in step a), the organic base is selected from morpholine, N-methylmorpholine, 1,1,3,3-tetramethylguanidine and mixtures thereof.

4. The process according to claim 1, wherein, in step b), the organic solvent for the resolution of the diastereoisomeric mixture of ethyl 5(R,S)-methyl-2-oxo-4(R)-phenylpyrrolidin-3(S)-carboxylate by crystallization is selected from methanol, ethanol, iso-propanol and mixtures thereof.

5. The process according to claim 1, wherein, in step b), the base for the hydrolysis of ethyl 5(S)-methyl-2-oxo-4(R)-phenylpyrrolidin-3(S)-carboxylate is selected from sodium hydroxide and potassium hydroxide.

6. The process according to claim 1, wherein, in step b), the decarboxylation of 5(S)-methyl-2-oxo-4(R)-phenylpyrrolidin-3(S)-carboxylate is carried out in an isopropyl acetate solution in the presence of para-toluenesulfonic acid at a temperature between 50° and 88° C.

7. The process according to claim 1, wherein, in step c), the sodium ion is introduced in the amide group of 5S-methyl-4R-phenylpyrrolidin-2-one by sodium hydride or sodium ethylate.

8. The process according to claim 1, wherein, in step d), the haloacetic acid ester is selected from bromoacetic acid ester and chloroacetic acid ester.

9. The process according to claim 1, wherein, in step e), the amidation of ethyl 2-(5S-methyl-2-oxo-4R-phenyl-pyrrolidin-1-yl)-acetate is carried out in aqueous ammonia or in a mixture of aqueous ammonia and a suitable organic solvent.

10. The process according to claim 1, wherein, in step e), the amidation of ethyl 2-(5S-methyl-2-oxo-4R-phenyl-pyrrolidin-1-yl)-acetate is carried out in a suitable organic solvent by its saturation with gaseous ammonia.

11. The process according to claim 9, wherein the organic solvent is selected from methanol, ethanol, propanol, chloroform, methylene chloride; ethyl acetate and 1,4-dioxane.

12. The process according to claim 10, wherein the organic solvent is selected from methanol, ethanol, propanol, chloroform, methylene chloride; ethyl acetate and 1,4-dioxane.

* * * * *

UNITED STATES PATENT AND TRADEMARK OFFICE
CERTIFICATE OF CORRECTION

PATENT NO.        : 8,791,273 B2                                Page 1 of 1
APPLICATION NO.   : 13/508184
DATED             : July 29, 2014
INVENTOR(S)       : Ivars Kalvins et al.

It is certified that error appears in the above-identified patent and that said Letters Patent is hereby corrected as shown below:

In the Claims

Column 10, Line 13, Claim 1:   "sodium on" should be --sodium ion--.

Column 10, Line 14, Claim 1:   "d)alkylation" should be --d)N-alkylation--.

Column 10, Line 26, Claim 3:   "tetramethylguanidine" should be --tetramethylquanidine--.

Signed and Sealed this
Twenty-fifth Day of November, 2014

Michelle K. Lee
*Deputy Director of the United States Patent and Trademark Office*